(12) United States Patent
Zhu et al.

(10) Patent No.: US 8,144,829 B2
(45) Date of Patent: Mar. 27, 2012

(54) CONE-BEAM CT IMAGING SCHEME (75) Inventors: Lei Zhu, Mountain View, CA (US); Lei Xing, Palo Alto, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 452 days.

(21) Appl. No.: 12/380,585

(22) Filed: Feb. 27, 2009

(65) Prior Publication Data
US 2009/0225932 A1 Sep. 10, 2009

Related U.S. Application Data (60) Provisional application No. 61/067,514, filed on Feb. 27, 2008.

(51) Int. Cl.
*A61B 6/03* (2006.01)
(52) U.S. Cl. ............................................. 378/7; 382/131
(58) Field of Classification Search ....... 378/7; 382/131
See application file for complete search history.

(56) References Cited

U.S. PATENT DOCUMENTS

| | | | | |
|---|---|---|---|---|
| 5,068,887 | A * | 11/1991 | Hughes | 378/170 |
| 6,618,466 | B1 | 9/2003 | Ning | |
| 6,748,047 | B2 * | 6/2004 | Gonzalez Trotter et al. | 378/62 |
| 7,308,072 | B2 | 12/2007 | Rührnschopf | |
| 2006/0067480 | A1 * | 3/2006 | Juschka et al. | 378/150 |
| 2006/0088140 | A1 | 4/2006 | Fahrig | |
| 2007/0086560 | A1 * | 4/2007 | Kia et al. | 378/7 |
| 2007/0280408 | A1 | 12/2007 | Zhang | |
| 2008/0025458 | A1 * | 1/2008 | Virshup et al. | 378/6 |
| 2008/0080663 | A1 | 4/2008 | Haerer | |
| 2009/0067576 | A1 * | 3/2009 | Maltz | 378/65 |
| 2009/0310835 | A1 * | 12/2009 | Kaus et al. | 382/128 |

FOREIGN PATENT DOCUMENTS

FR 2864685 A1 * 7/2005

OTHER PUBLICATIONS

Thilmann et al., Correction of patient positioning errors based on in-line cone beam CTs: clinical implementation and first experiences, May 24, 2006, Radiation Oncology, vol. 1, pp. 16-25.*
Siewerdsen et al., A simple, direct method for scatter estimation and correction in digital radiography and cone-beam CT, 2006, Medical Physics, vol. 31, No. 1, pp. 187-197.*
Jarry et al., Characterization of scattered radiation in kV CBCT images using Monte Carlo simulations, 2006, Medical Physics, vol. 33, No. 11, pp. 4320-4329.*

(Continued)

*Primary Examiner* — Edward Glick
*Assistant Examiner* — John Corbett
(74) *Attorney, Agent, or Firm* — Lumen Patent Firm (57) ABSTRACT

A general imaging scheme is proposed for applications of CBCT. The approach provides a superior CBCT image quality by effective scatter correction and noise reduction. Specifically, in its implementation of CBCT imaging for radiation therapy, the proposed approach achieves an accurate patient setup using a partially blocked CBCT with a significantly reduced radiation dose. The image quality improvement due to the proposed scatter correction and noise reduction also makes CBCT-based dose calculation a viable solution to adaptive treatment planning.

16 Claims, 4 Drawing Sheets

OTHER PUBLICATIONS

Moore et al. ("Cone beam CT with zonal filters for simultaneous dose reduction, improved target contrast and automated set-up in radiotherapy", 2006, Physics in Medicine and Biology, vol. 51, pp. 2191-2204.*

Hansen et al., Extraction of primary signal from EPIDs using only forward convolution, 1997, Medical Physics, vol. 24, No. 9, pp. 1477-1484.*

Zhu et al., Scatter Correction Method for X-Ray CT Using Primary Modulation: Theory and Preliminary results, Dec. 12, 2006, IEEE Transactions on Medical Imaging, vol. 25, No. 12, pp. 1573-1587.*

Lu et al., Analytical Noise Treatment for Low-Dose CT Projection Data by Penalized Weighted Least-Square Smoothing in the K-L Domain 2002, SPIE, vol. 4682, pp. 146-152.*

Wang et al., Penalized Weighted Least-Squares Approach to Sinogram Noise Reduction and Image Reconstruction for Low-Dose X-ray Computed Tomography, Oct. 2006, IEEE Transactions on Medical Imaging, vol. 25, No. 10, pp. 1272-1283.*

Wagner et al., Dual-energy x-ray projection imaging: Two sampling schemes for the correction of scattered radiation, 1988, Medical Physics, vol. 15, No. 5, pp. 732-748.*

Moore et al., Cone beam CT with zonal filters for simultaneous dose reduction, improved target contrast and automated set-up in radiotherapy, 2006, Physics in Medicine and Biology, vol. 51, pp. 2191-2204.*

Colbeth et al., Flat panel CT detectors for sub-second volumetric scanning, 2005, Proceedings of the SPIE, Medical Imaging 2005: Physics of Medical Imaging, vol. 5745, pp. 387-398.*

Bushberg et al., The Essential Physics of Medical Imaging, 2002, Published by Lippincott Williams & Wilkins, Second Edition, ISBN 0-683-30118-7, pp. 346-356.*

* cited by examiner

CONE-BEAM CT IMAGING SCHEME

CROSS-REFERENCE TO RELATED APPLICATIONS

This application claims priority from U.S. Provisional Patent Application 61/067,514 filed Feb. 27, 2008, which is incorporated herein by reference.

FIELD OF THE INVENTION

The present invention relates generally to methods and devices for x-ray cone-beam computed tomography (CBCT). More specifically, it relates to techniques for improving image quality in CBCT applications such as radiation therapy.

BACKGROUND

Radiation therapy is the use of ionizing radiation in the treatment of cancer. External beam radiotherapy uses diagnostic imaging techniques for treatment planning. A conventional preparation procedure for radiation therapy includes a prior computed tomography (CT) scan using a multi-detector CT (MDCT) scanner for treatment planning and a three-dimensional cone-beam CT (CBCT) scan for patient setup. A three-dimensional registration is performed on the planning CT and the CBCT data to derive appropriate shifts and rotations for patient positioning. CBCT can also be used to calculate the delivered radiation dose, but this application is not commonly applied mainly due to the inferior image quality of CBCT.

The treatment typically involves one or two CBCT scans every day for four to six consecutive weeks, resulting in a large undesired radiation dose to the patient. Reducing the CBCT radiation dose decreases secondary cancer risk, but it generally results in degraded image quality and reduced image reconstruction accuracy. In addition, x-ray scattering during CBCT imaging causes severe shading and streak artifacts in reconstructed CBCT images, reducing the accuracy of imaging-based procedures during radiation treatment. Since the scatter signal increases as the illuminated volume increases, the scatter problem is especially severe in CBCT systems, which use a large illumination beam. Moreover, known techniques for scatter compensation increase noise in the image. In view of these problems, there is a need for improved techniques for CBCT imaging in radiation therapy.

SUMMARY OF THE INVENTION

In one aspect, the present invention provides a technique for CBCT imaging that significantly reduces both scattering effects and undesired radiation dose to the patient while providing high image quality and accurate image registration for patient positioning and dose calculation. By positioning a patterned lead sheet between the CBCT beam source and the patient, many of the x-rays from the CBCT beam source are blocked, resulting in an incomplete projection image on the CBCT detector. In a preferred embodiment, the beam blocking sheet includes several rectangular lead strips, producing a sequence of parallel illuminated slices corresponding to the gaps between the strips. Since the radiation is partially blocked by the strips, the dose delivered to the patient is significantly reduced, with an additional benefit of reduced scatter signals and increased image quality of the illuminated slices. Although the projection image is incomplete, sufficient registration is still possible using the illumined slices.

In one aspect, an improved method for medical imaging is provided. The method includes performing a multi-detector computed tomography (MDCT) scan of a patient to produce MDCT scan data and reconstructing MDCT image slices from the MDCT scan data. The method also includes performing a cone-beam computed tomography (CBCT) scan of the patient using a CBCT beam source to produce CBCT scan data and reconstructing CBCT image slices from the partially blocked CBCT scan data. Significantly, the CBCT scan comprises positioning a patterned lead sheet between the CBCT beam source and the patient to partially block x-rays from the CBCT beam source. The method also includes performing 3D rigid registration of the MDCT image slices and the CBCT image slices to obtain fused reconstructed images of the patient for use in radiation treatment planning.

In a preferred implementation, the patterned lead sheet is made of rectangular lead strips whose widths are at least 5 mm and which are separated to form gaps at least 2 mm wide. Preferably, the patterned lead sheet is sufficiently thick to completely block x-rays from passing through the sheet and reduces x-rays reaching the patient from the CBCT beam source by a factor of at least six.

The reconstruction of the CBCT image slices preferably includes correcting for scatter using an estimated scatter derived from a stored scatter distribution for the patient. Several alternative techniques may be used for estimating scatter. According to one technique, the stored scatter distribution for the patient is derived from a previous partially blocked CBCT scan of the patient, e.g., from measured x-ray signals in shadow regions produced in the previous CBCT scan of the patient using the patterned lead sheet. According to an alternate technique, the stored scatter distribution for the patient is derived from a previous MDCT scan of the patient. The stored scatter distribution for the patient is derived by converting Hounsfield unit (HU) CT values of the previous MDCT scan into electron density, and then performing a Monte Carlo (MC) simulation to obtain the stored scatter distribution. According to still another alternate technique, the stored scatter distribution for the patient is derived from a previous MDCT scan of the patient by registering the CBCT scan data with the previous MDCT scan, forward projecting data from the previous MDCT scan of the patient to simulate primary signals in a CBCT scan, and subtracting the simulated primary signals from the CBCT scan data to obtain the stored scatter distribution.

Several alternative techniques may be used for correcting scatter using the scatter estimate. According to one technique, correcting for scatter includes registering the previous MDCT scan or partially blocked CBCT reconstruction with an unblocked CBCT reconstruction, modifying the stored scatter distribution according to the registration, and subtracting the modified scatter distribution from the CBCT scan data. According to an alternate technique, correcting for scatter includes using the scatter estimates together with a sophisticated kernel-based scatter model. According to yet another alternate technique, reconstructing the CBCT image slices includes correcting for scatter by reconstructing the CBCT image slices without scatter correction, registering the reconstructed CBCT image slices with the MDCT image slices, and performing a Monte Carlo simulation on the MDCT image slices to estimate and correct for scatter in the reconstructed CBCT image slices.

Preferably, reconstructing the CBCT image slices includes reducing noise introduced by scatter correction. The noise may be reduced by applying a penalized weighted least-squares (PWLS) technique to CBCT image projection data. The PWLS technique may use a cost function involving a variance of scatter-corrected line integral data $q_c$ given by $\text{var}(q_c) = p_m/(p_m - s_e)^2$, where $p_m$ is measured image projection data and $s_e$ is a scatter estimate.

DETAILED DESCRIPTION

Figure 1:
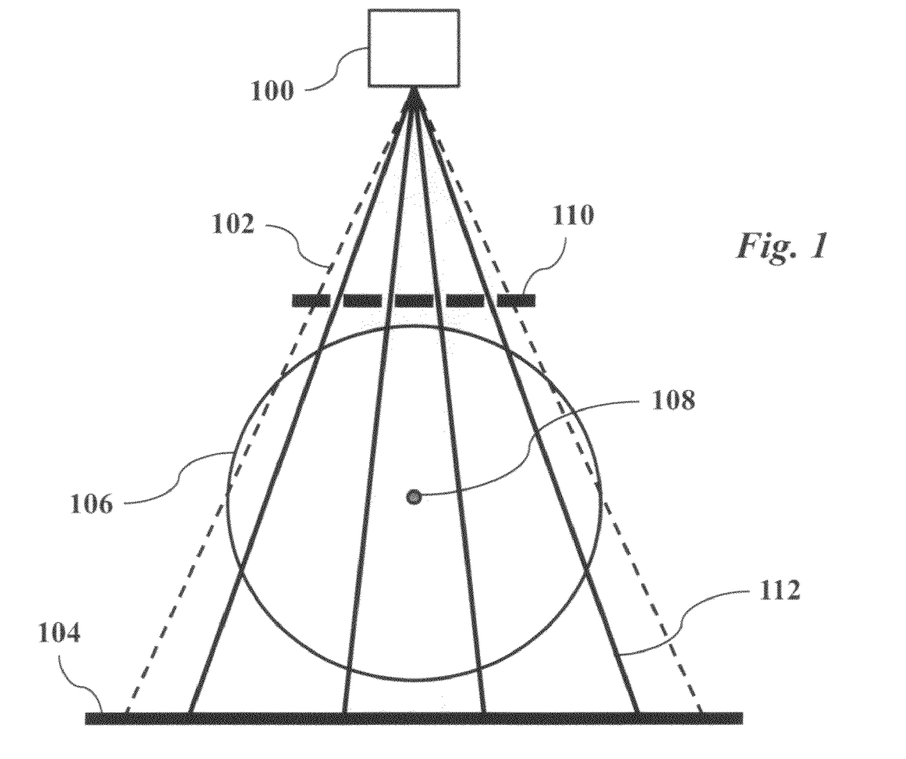
FIG. 1 is a cross-sectional side-view illustration of a modified CBCT system according to an embodiment of the invention.

A cone-beam CT (CBCT) imaging system for the treatment planning of radiation therapy is shown in FIG. 1. As with a conventional CBCT system, an x-ray source 100 generates a cone beam 102 which creates a projection image on detector 104 after passing through a patient 106. The system is designed to rotate around axis 108 during the imaging process. A modified CBCT system according to an embodiment of the invention also includes a patterned beam blocking sheet 110 positioned between source 100 and patient 106 so that a significant portion of the x-rays 102 from source 100 are blocked by the sheet 110 and do not reach patient 106, significantly reducing the radiation dose to the patient. Gaps in the sheet 110 allow portions of the beam 102, such as portion 112, to pass through the sheet and illuminate the patient 106 and detector 104.

As is apparent, this modified system is easily obtained from an existing system by adding an inexpensive patterned plate. No other modifications to the existing system are required. For example, a CBCT imaging system according to one embodiment may be obtained by adding a beam blocking sheet to a Varian Acuity CT simulator (Varian Medical Systems, Palo Alto, Calif.). In such a system, the x-ray tube operates at 125 kVp voltage and 80 mA with the pulse width at each projection angle of 25 ms. A bow-tie filter is used to maintain a more uniform photon statistics across the field of view (FOV). Data from a 360-degree scan includes about 685 projections with an angle interval of about 0.5 degrees. The dimension of each acquired projection image is 397.3 mm by 298.0 mm, containing 1024 by 768 pixels. With a source-to-axis distance (SAD) of 1000 mm and source-to-imager distance (SID) of 1500 mm, the FOV is around 250 mm (diameter) in the transverse plane with a full-fan mode. In a half-fan mode, the flat-panel detector is shifted by approximately 160 mm, and the FOV is increased to 500 mm. The FOV in the longitudinal direction is 170 mm. Using the partial CBCT data, reconstructed images are still complete for certain slices in the axial direction.

Figure 2:
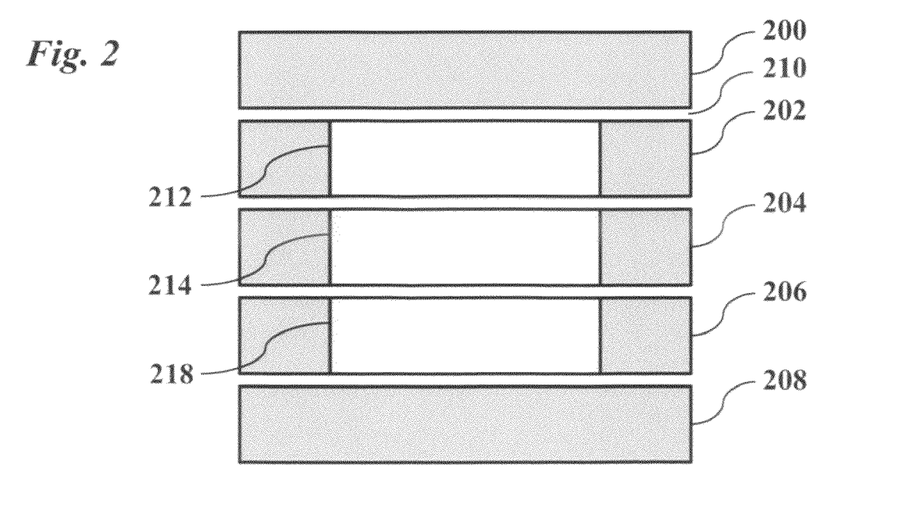
FIG. 2 is a cross-sectional top-view illustration of a beam blocking sheet made of rectangular lead strips according to an embodiment of the invention.

FIG. 2 shows a top-view cross-section of a beam blocking sheet according to one embodiment. The sheet is composed of several rectangular strips, 200, 202, 204, 206, 208, arranged in parallel with gaps, such as gap 210, separating them. This arrangement produces a pattern of parallel slits through which x-rays may pass. Preferably, the ratio of illuminated area on the detector to the total detector area is approximately 1 to 6, corresponding to a dose reduction factor of approximately 6. For example, in one embodiment, the strips are 10 mm wide and separated by 2 mm gaps. The sheet of lead strips may be mounted on the outside surface of the collimator, at a distance of approximately 400 mm from the x-ray focal spot, and oriented parallel to the plane of the source trajectory.

In other embodiments, the beam blocking sheet 110 may have a different pattern to produce different sizes or shapes of blocked and illumined areas. For example, the sheet may have an array of square or circular holes or an array of square or circular blocking elements. Such patterns could provide a more complete image of the entire object than the rectangular strips, while still reducing the radiation dose. Image reconstruction for these more complicated patterns, however, would be more complicated than for rectangular strips. The strip pattern has the advantage that current reconstruction algorithms may be used.

The lead strips 200, 202, 204, 206, 208 in beam blocking sheet 110 are preferably thick enough to completely block incident x-rays. For example, the strips may have a thickness of approximately 2 mm. In the diagnostic energy range of CBCT, these lead strips attenuate over 99% of the x-ray photons.

In other embodiments, however, the x-ray attenuation of the inserted blocking sheet can be less than 100%. For example, the rectangular strips may have an attenuation of 90% or 80%. In addition, the attenuation level may be uniform throughout the sheet, or it may be non-uniform. For example, there may be relatively high attenuation in the portions of the blocking sheet where x-ray attenuation due to the image object is small (e.g., along the edges) while relatively lower attenuation in the portions of the blocking sheet where x-ray attenuation due to the image object is large (e.g., at or close to the center of the field of view, near the rotational axis). FIG. 2 illustrates this idea with portions 212, 214, 218 of strips 202, 204, 206, respectively, which have reduced attenuation. The advantage of producing more blocking around the edges is that scatter will be more uniform, providing higher quality images. However, a non-uniform attenuation by the blocking sheet may require more complicated image reconstruction techniques.

Figure 3:
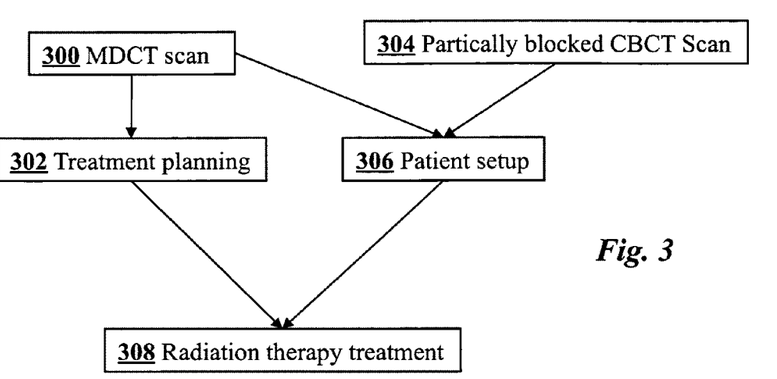
FIG. 3 is a flow chart showing a work flow for a radiation therapy procedure according to an embodiment of the invention.

FIG. 3 is a flow chart showing a work flow for a radiation therapy procedure according to a preferred embodiment of the invention. In step 300, an MDCT scan of a patient is performed to produce MDCT scan data and reconstructed MDCT image slices. This MDCT information is used in a treatment planning step 302 as in the conventional procedure. Conventional MDCT systems may be used. For example, the planning CT images may be acquired by a Discovery ST PET/CT scanner (Discovery ST/LightSpeed 8-slice; General Electric Medical Systems). For CT scans, it has a 50 cm trans-axial field of view (FOV) and the detector coverage in the cranial-caudal direction is 2 cm. The detector arrays are on an arc concentric to the X-ray source with a distance of 949.1 mm. The distance from the rotation center to the X-ray source is 541.0 mm. The CT images are acquired using step-and-shoot technique (cine mode). The tube current is 300 mA, the tube voltage is 120 kV p, and the gantry rotation time is 1 s. The reconstruction slice thickness is 1.25 mm.

In step 304, a CBCT scan of the patient is performed to produce CBCT scan data. Instead of a conventional CBCT scan, however, this step involves positioning a patterned lead sheet between the CBCT beam source and the patient to partially block x-rays from the CBCT beam source using the modified system described above in relation to FIGS. 1 and 2. This improved method decreases the illuminated volume of the patient, and greatly reduces the scatter signals. Consequently, in the illuminated slices, it achieves a better image quality as compared to the conventional CBCT scan.

In step 306, the MDCT scan data and partially blocked CBCT scan data are reconstructed and then combined to perform 3D rigid registration of the MDCT image slices and the CBCT image slices for patient setup. Due to the x-ray blocking of the inserted lead strips, regular reconstruction of the CBCT image slices is performed only on a limited number of slices where the patient was illuminated. To compensate for the missing data of the reconstructed image, 3D registration of the MDCT data and the partially blocked CBCT data is performed in the domain of the reconstructed image or in the domain of the projection data using existing data registration methods. The blocked slices are compensated for using the registered 3D MDCT data. This is a unique feature of the method: the prior MDCT data is used to enhance the quality of partially blocked CBCT images. In the conventional procedures, the prior MDCT data and the CBCT data are used independently. The present method is based on the insight that in the patient set-up of radiation therapy, a conventional CBCT scan acquires more information than necessary to derive the patient geometry. Therefore, data acquisition can be significantly reduced to save radiation dose.

Registration may be performed using conventional methods such as the Insight Toolkit (ITK). To improve the registration accuracy, the reconstructed images preferably are first thresholded and only the bone structures are used for registration. The cost function for minimization may be chosen to be the mean square pixel-wise difference between the volumes. The registration uses versors (i.e., a unit quaternion corresponding to a directed great circle arc) and a 3D translational vector to describe the 3D rigid motion. The optimization method is a simple gradient descent search algorithm, which decreases the search step size as the optimization progresses and oscillates around a minima of the cost function. Furthermore, to speed registration, a multi-resolution image pyramid may be used which first registers low resolution versions of the datasets, and then subsequently registers higher resolution versions. Initial conditions may be chosen by first placing both datasets in the same coordinate system and aligning their center of masses. After approximately 100 steps, the step size may be decreased below a chosen threshold value and the registration completed.

In step 308, the treatment planning and patient setup and dose optimization information is used for radiation therapy treatment as in the conventional preparation of radiation therapy. Based on the registration parameters, the patient is set up accordingly before the treatment, to have a best geometric match to the treatment plan.

In addition to reducing the undesired radiation dose to the patient and improving image quality by reducing the scatter signals in the CBCT scan, this method allows accurate CBCT-based dose calculation by mapping the electron density information from MDCT to the fused CBCT images. The existing software in commercial systems can still be used without modifications for the reconstruction. The present method also requires no additional training for physicians. Although this modified CBCT system and associated method is designed primarily for radiation oncology, the technique may also be applied to other medical procedures where repeated CBCT is required.

Scatter is a serious problem in CBCT and is considered as one of the fundamental limitations of CBCT image quality. The use of a blocking sheet is able to reduce the effects of scatter at the price of missing slices in the reconstructed image. In CBCT applications where a complete image of the object is desired further scatter correction is still needed. Accordingly, embodiments of the invention preferably include methods for scatter correction. In applications such as CBCT in radiation therapy where repetitive CBCT scans on the same object (patient) are applied, the inventors have recognized that patient-specific scatter data from a prior CBCT imaging can be measured and stored. This scatter data can then be used to correct for scatter in subsequent on-treatment CBCT projection data, provided it is suitably transformed to take into consideration the on-treatment patient position. In the context of the method discussed in relation to FIG. 3, the reconstruction of the CBCT image slices in patient setup 306 preferably includes correcting for scatter using an estimated scatter derived from a stored scatter distribution for the patient.

Several alternative techniques may be used for estimating scatter. According to one technique, partially blocked CBCT scan data is used for the scatter measurement. The whole-field scatter distribution can be estimated from the detected signals in the shadow region using low-pass filtering and extrapolation. In other words, the stored scatter distribution for the patient is derived from a previous partially blocked CBCT scan of the patient. For example, the measured x-ray signals in shadow regions produced by lead blocking strips are detected and used to derive the scatter estimate. Inside the strip shadows on the detector, no primary signals are detected and the measured signals provide scatter samples. Assuming the insertion of the lead strips does not greatly perturb shape of the scatter distributions in the CB projection and scatter contains dominant low-frequency signals, we can estimate the scatter distribution of the whole field in a regular CB projection using the measured scatter samples. To avoid the edge effect of the strips, only the measured data inside the central one third of the strip shadows are used in the scatter measurement. The data inside one strip shadow are first averaged in the longitudinal direction to reduce the noise in the measurement. A moving-average filtering with a width of 9 detector pixels is then applied in the lateral direction to further smooth the scatter distribution. The obtained one-dimensional profiles are the measured scatter at the centers of the strip shadows. A cubic spline interpolation/extrapolation is then carried out to estimate the scatter distribution of the whole detector area. Assuming the scatter magnitude is proportional to the illuminated volume, to obtain a scatter estimate in a regular CBCT projection, the scatter estimate in the partially blocked CBCT projection is finally magnified by the ratio of the total detector area to the illuminated detector area.

According to an alternate technique, the stored scatter distribution for the patient is derived from a previous MDCT scan of the patient. The pre-scan MDCT data are routinely acquired in radiation therapy for treatment planning. First the HU CT values are converted into electron density, and then a Monte Carlo (MC) simulation is performed to obtain scatter distributions. In other words, the stored scatter distribution for the patient is derived by converting Hounsfield unit (HU) CT values of the previous MDCT scan into electron density, and then the stored scatter distribution is obtained from a Monte Carlo (MC) simulation.

According to still another alternate technique, the stored scatter distribution for the patient is derived from the pre-scan MDCT data and projections in a regular CBCT scan. The scatter estimate is derived by registering the CBCT scan data with the previous MDCT scan, where the MDCT data is calibrated to have the HU values matching those of the CBCT, forward projecting data from the previous MDCT scan of the patient to simulate primary signals in a CBCT scan, and subtracting the simulated primary signals from the CBCT scan data to obtain the stored scatter distribution.

Once the scatter distribution estimate has been stored, it can then be used in subsequent CBCT scans to correct the scatter. Several alternative techniques may be used for correcting scatter using the scatter estimate. According to one technique, scatter may be corrected by registering the stored scatter distribution with a blocked or unblocked CBCT reconstruction, modifying the stored scatter distribution according to the registration, and subtracting the modified scatter distribution from the CBCT scan data. Two variants of this approach may be used depending on how the estimate of scatter was derived. If the method of partially blocked CBCT was used, the measured scatter data may be modified according to the patient registration information and used for scatter correction in the subsequent CBCT scans. This technique is shown in the flow diagram of FIG. 4. In step 400 a partially blocked CBCT scan is performed and the scatter estimated and then stored in step 402. During treatment, CBCT scan is performed in step 404 and corrected for scatter in step 406 using the scatter distribution estimate stored in step 402. As will be discussed later, after scatter correction, scatter noise reduction is preferably performed in step 408. FIG. 5 is an illustrative flow chart showing a detailed work flow for a scatter estimation and correction technique using partially blocked CBCT projections 500 to derive a scatter estimate 502 which is then registered with a CBCT projection 504 at treatment time to obtain registered scatter estimate 506 and produce scatter corrected projections 508. A scatter corrected CT image 510 is then reconstructed.

Figure 6:
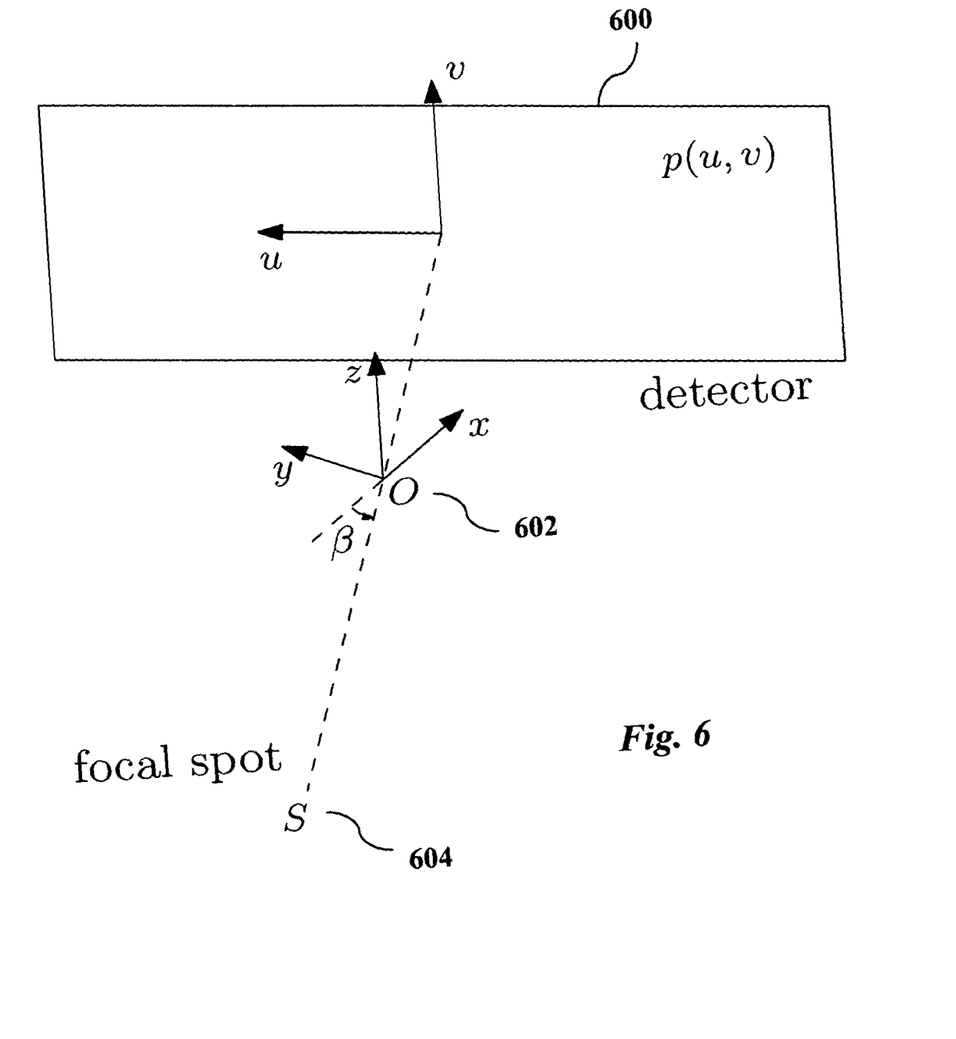
FIG. 6 is a perspective diagram illustrating parameters and coordinate systems used in a patient transformation according to an embodiment of the invention.

Scatter distributions for the same patient change in different CBCT scans, due to different patient positions. Even if the same imaging parameters are used and a rigid transformation of the patient is assumed for different scans, an accurate relationship between scatter distributions and the patient position is in general very complicated. However, an approximate formula may be used to calculate the scatter distribution of a regular CB projection from the pre-measured scatter distributions using a registration of the partially blocked CBCT reconstruction and the regular CBCT reconstruction. In particular, we approximate the scatter distributions after a patient translation by shifting the original scatter distributions as if in a parallel-beam geometry. Equivalently, we assume the scatter distribution shifts together with the projection of rotation center on the detector. The distance of shifting is calculated as the patient translation in the direction parallel to the detector multiplied by a magnification factor determined by the CB geometry. We also assume the patient rotation about the x and y axes is very small. Based on these assumptions, the following estimation formula may be derived:

$$S_e(u,v,\beta)=S_m(u+t_u,v+t_v,\beta+\gamma_z),$$

where $S_m$ is the measured scatter obtained from the partially blocked CBCT projection data, $S_e$ is the estimated scatter distribution, u and v are the lateral and longitudinal detector coordinates, $\beta$ is the projection view angle, $t_u$ and $t_v$ are the patient translations in the u-v plane, and $\gamma_z$ is the patient rotation about the z-axis, which is aligned with the v-axis. FIG. 6 is a perspective diagram illustrating parameters and coordinate systems used, showing the u-v plane of the detector 600, the x-y-z axes 602 and focal spot 604. The above formula for $S_e$ shows that the scatter can be estimated by shifting the pre-measured scatter distributions in all three directions. A cubic spline extrapolation is used when the index of estimated scatter is outside the space of the pre-measured scatter.

Figure 4:
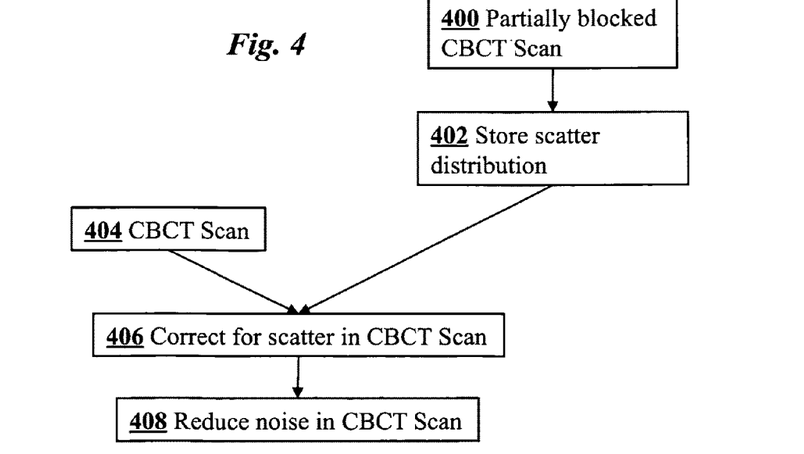
FIG. 4 is a flow chart showing a work flow for a scatter correction technique according to an embodiment of the invention.
Figure 5:
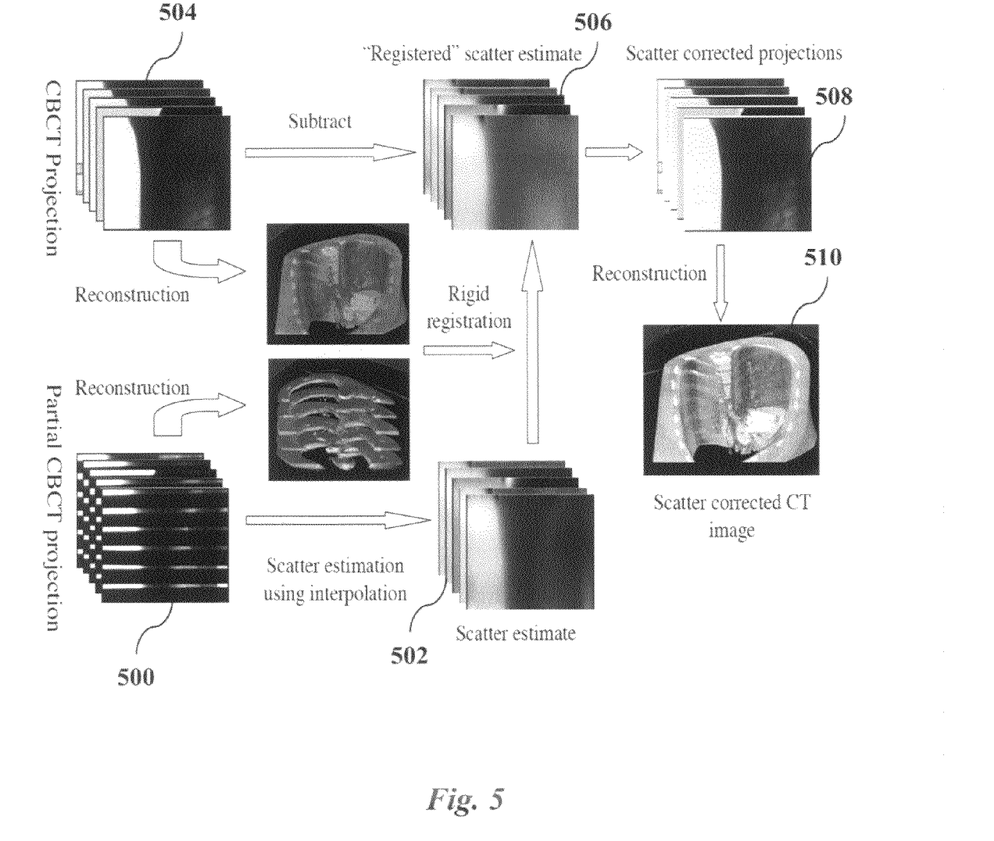
FIG. 5 is a flow chart showing a detailed work flow for a scatter correction technique according to an embodiment of the invention.

If MC simulation on the pre-scan MDCT data or the method of forward projecting MDCT data was used to derive the scatter estimate, the technique of FIG. 4 may be modified. In particular, a regular CBCT and the MDCT scan data are used to calculate patient rigid transformation and the scatter estimates are pre-computed using MC simulation. A partially blocked CBCT is not used in this case.

Another method for scatter correction includes using the scatter estimates together with a sophisticated kernel-based scatter model. When the scatter estimation is less accurate due to organ deformation, the scatter in a regular scan can be removed using the scatter estimates together with a sophisticated kernel-based scatter model. Existing analytical correction methods using a scatter model, such as kernel-based deconvolution method, may be used. These methods typically have several user-defined algorithm parameters, such as kernel widths and magnitudes, which need to be tuned carefully for different patients and different imaging geometries. Using the scatter estimates available using partially blocked beams, the algorithm parameters can be optimized on a known patient geometry using an iterative algorithm. A scatter correction can then be performed on a regular CBCT scan on the same patient. The use of prior knowledge significantly simplifies the kernel-based scatter correction method and optimizes its performance.

If there is sufficient available computing power, scatter can be estimated directly from the regular CBCT data using the pre-scan MDCT data without pre-computing scatter data. In other words, the scatter can then be corrected by reconstructing the CBCT image slices without scatter correction, registering the reconstructed CBCT image slices with the MDCT image slices using a rigid or deformable registration, and performing a Monte Carlo simulation on the MDCT image slices to estimate and correct for scatter in the reconstructed CBCT image slices from the regular scan. When the scatter estimation is inaccurate due to errors in the image registration, this method can also be combined with the kernel-based method described to improve the scatter correction performance.

Scatter correction alone does not provide satisfactory images in CBCT because the gain from the scatter reduction processing is accompanied by overwhelming noise-related artifacts. Thus, reconstructing the CBCT image slices preferably includes reducing noise introduced by scatter correction. Most existing scatter correction techniques use post-processing methods on the scatter contaminated projection images to improve the reconstruction accuracy. These methods, however, only partially solve the problem caused by scatter and do not remove the high frequency components of the scatter signal. After appropriately analyzing the noise in images that have been subjected to scatter correction techniques, the present inventors have developed a novel technique for noise reduction due to scatter correction. To understand this scatter noise problem and its solution, consider the following analysis.

There are two major types of noise in x-ray projection images. The first type is the image-independent noise due to the electrical and round-off error, which can be treated as Gaussian noise. The second type of noise is the image-dependent noise due to the statistical fluctuation of the x-ray photons that exit an object, which can be treated as Poisson noise. The Gaussian noise is assumed to be relatively small as compared with the Poisson noise, so only the Poisson noise will be considered.

In what follows, s and p denote the detected scatter signal and primary signal, respectively, at a detector pixel, while S and P denote their respective mean values and $n_s$ and $n_p$ denote their respective statistical noises. Since these signals are Poisson distributed, we have s≈Poisson(S) and p≈Poisson (P). In addition, since the point spread function of the scatter is broad and smooth, s is independent of p. Consequently, $(s+p) \approx$ Poisson(S+P). In addition, we know that $s = S + n_s$ and $p = P + n_p$. So, due to Poisson statistics, we have $\mathrm{var}(n_s) = S$ and $\mathrm{var}(n_p) = P$.

The line integral image without scatter correction is given by $$q = \ln(I_0) - \ln(s+p),$$

where $I_0$ is the incident photon intensity. Thus, to first order, $$q \approx \ln(I_0) - \ln(S+P) - (n_s + n_p)/(S+P),$$

using the Taylor expansion at (S+P). Now since $I_0$ is typically large, the noise associated with $\ln(I_0)$ can be ignored. And assuming $(n_s + n_p)$ is small, the noise of q and its variance may be approximated by $$n_{nc} \approx -(n_s + n_p)/(S+P)$$

and $$\mathrm{var}(n_{nc}) \approx \mathrm{var}(n_s + n_p)/(S+P)^2 \approx 1/(S+P),$$

respectively.

When an effective scatter correction algorithm is applied, the scatter mean value S is removed from the signal while the high frequency noise $n_s$ remains. Thus, the line integral image with scatter correction is given by $$q_c = \ln(I_0)\ln(s+p-S)\ln(I_0)\ln(P) - (n_s+n_p)/P.$$

Similarly the noise of $q_c$ and its variance may be approximated by $$n_c \approx -(n_s + n_p)/P$$

and $$\mathrm{var}(n_c) \approx (1+S/P)^2/(S+P),$$

respectively. Therefore, the ratio of the variances of $n_c$ and $n_{nc}$ is $$\mathrm{var}(n_c)/\mathrm{var}(n_{nc}) \approx (1+S/P)^2.$$

This ratio shows that the noise is magnified after a scatter correction is performed on the projection image. Moreover, since the noise-free scatter signal S is spatially much smoother than the noise-free primary signal P, the spatial distribution of S/P is typically non-uniform. As a result, the noise variance magnification across the projection image can vary significantly, e.g., by almost two orders of magnitude in many cases. This non-uniform noise magnification not only increases the noise level in the reconstructed image but also results in local streaking artifacts.

Based on the above analysis, a noise reduction method may be developed, as follows. The technique uses a penalized weighted least-squares (PWLS) technique which is modified based on the noise property $\mathrm{var}(n_c)$ of the scatter corrected image as derived above. The PWLS technique is a statistics-based technique that aims to estimate the ideal linear integrals by minimizing the PWLS objective function defined by $$\phi(q_c^*) = (q_c - q_c^*)^T \Sigma^{-1} (q_c - q_c^*) + \beta R(q_c^*),$$

where $q_c$ is the vector of the scatter-corrected line integral data whose elements range over the pixel values $q_c$, and $q_c^*$ is the vector of noise-reduced line integral data to be estimated.

The matrix $\Sigma$ is a diagonal matrix whose i-th element is the variance of $q_c$ at detector pixel i, which may be approximated by $$\mathrm{var}(q_c) \approx p_m/(p_m - s_e)^2,$$

where $p_m$ is the measured projection data before scatter correction and application of the logarithm, and where $s_e$ is the scatter estimate.

The first term of the objective function is represents a weighted least-squares criterion while the second term is a smoothness penalty controlled by smoothing parameter $\beta$ which determines the degree of agreement between the estimated and measured data, i.e., it represents a tradeoff between reconstruction accuracy and resolution loss. In adaptive radiation therapy using CBCT a large value for $\beta$ is preferred because reconstruction accuracy is more important than resolution. The function R is a quadratic function of the data. For example, the function R may be given by $$R(q) = \Sigma_i \Sigma_n w_{i,n} (q_i - q_n)^2,$$

where the index i ranges over the four nearest neighbors around pixel i and $w_{i,n}$ is the weight for neighbor n of pixel i. The expression $q_i - q_n$ is the difference between the value of line integral image q at pixel i and the value at pixel n. To preserve the edge information, anisotropic weights are preferably used. For example, the weight of the neighbor n may be determined by the magnitude of the difference between neighbors and the pixel i of concern:

$$w_{i,n} = \exp(-(q_i - q_n)^2/\delta),$$

where $\delta$ is a user-defined parameter that controls the strength of edge preservation. The parameter 6 may be chosen preferably such that 90% of the projection pixels have a gradient magnitude smaller than $\delta$.

The cost function $\phi$ models the first-order and second order statistics of the measurements and its minimization provides an optimal solution in a statistical sense. In practice, the objective function may be minimized efficiently using an iterative Gauss-Seidel updating strategy. If standard CBCT imaging parameters are used, the technique typically converges to an optimal solution after about 20 iterations. For example, the computation may be implemented on a 3.0 GHz processor, in which case each projection image can be processed for noise reduction in about 3 seconds.

Although this scatter noise reduction technique has been described in relation to particular scatter correction methods in the context of a CBCT radiation therapy scheme, it may be used more generally with any scatter correction methods.

Although the embodiments of this invention have been described in relation to applications to radiation therapy, it can also be used in other applications of CBCT to reduce the radiation dose and improve the image quality, such as C-arm CT.

The invention claimed is:

1. A method for medical imaging comprising:
   a) performing a multi-detector computed tomography (MDCT) scan of a patient to produce MDCT scan data;
   b) reconstructing MDCT image slices from the MDCT scan data;
   c) performing a cone-beam computed tomography (CBCT) scan of the patient using a CBCT beam source to produce CBCT scan data, wherein performing the CBCT scan comprises positioning a patterned lead sheet between the CBCT beam source and the patient to partially block x-rays from the CBCT beam source, such that the CBCT scan data is produced from a partially blocked CBCT beam;

d) reconstructing CBCT image slices from the CBCT scan data;
e) performing 3D rigid registration of the MDCT image slices and the CBCT image slices to obtain fused reconstructed images of the patient;
wherein the method further comprises:
storing a scatter distribution for the patient; and
correcting for scatter by using scatter estimates derived from the scatter distribution together with a kernel-based scatter model.

2. The method of claim 1 wherein the patterned lead sheet reduces x-rays reaching the patient from the CBCT beam source by a factor of at least six.

3. The method of claim 2 wherein the patterned lead sheet comprises rectangular lead strips arranged in parallel to produce a pattern of parallel slits through which x-rays may pass to produce a sequence of parallel illuminated slices corresponding to gaps between the strips.

4. The method of claim 3 wherein the rectangular lead strips are sufficiently thick to completely block x-rays from passing through the strips.

5. The method of claim 1 wherein the patterned lead sheet comprises an array of holes.

6. The method of claim 1 wherein the patterned lead sheet comprises an array of blocking elements.

7. The method of claim 1 further comprising deriving the scatter distribution for the patient from the CBCT scan data produced from the partially blocked CBCT beam.

8. The method of claim 7 wherein the scatter distribution for the patient is derived from measured x-ray signals in shadow regions of the CBCT scan data produced from the partially blocked CBCT beam.

9. The method of claim 1 further comprising deriving the scatter distribution for the patient from the MDCT scan data.

10. The method of claim 9 wherein the scatter distribution for the patient is derived by converting Hounsfield unit CT values of the MDCT scan data into electron density, and then performing a Monte Carlo (MC) simulation of the MDCT scan data to obtain the scatter distribution.

11. The method of claim 1 further comprising correcting for scatter in an unblocked CBCT scan of the patient by registering the MDCT scan data with an unblocked CBCT reconstruction, modifying the scatter distribution according to the registration, and subtracting the modified scatter distribution from unblocked CBCT scan data.

12. The method of claim 1 further comprising correcting for scatter in an unblocked CBCT scan of the patient by registering the reconstructed CBCT image slices from the CBCT scan data produced from the partially blocked CBCT beam with an unblocked CBCT reconstruction, modifying the scatter distribution according to the registration, and subtracting the modified scatter distribution from unblocked CBCT scan data.

13. The method of claim 1 wherein reconstructing CBCT image slices comprises correcting for scatter by reconstructing the CBCT image slices without scatter correction, registering the reconstructed CBCT image slices with the MDCT image slices, and performing a Monte Carlo simulation on the MDCT image slices to estimate and correct for scatter in the reconstructed CBCT image slices.

14. The method of claim 1 wherein reconstructing CBCT image slices comprises correcting for scatter, and reducing noise introduced by the correcting for scatter.

15. The method of claim 14 wherein reducing the noise comprises applying a penalized weighted least-squares (PWLS) technique to CBCT image projection data.

16. The method of claim 15 wherein the PWLS technique uses a cost function involving a variance of scatter-corrected line integral data $q_c$ given by $\text{var}(q_c) = p_m/(p_m - s_e)^2$, where $p_m$ is measured image projection data and $s_e$ is a scatter estimate.

* * * * *